United States Patent
Otaka et al.

(12) 
(10) Patent No.: US 7,026,340 B2
(45) Date of Patent: Apr. 11, 2006

(54) MALONONITRILE COMPOUNDS AND THEIR USE AS PESTICIDES

(75) Inventors: Ken Otaka, Iwaki (JP); Daisuke Oohira, Toyonaka (JP); Daisuke Takaoka, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 42 days.

(21) Appl. No.: 10/516,343

(22) PCT Filed: Jul. 7, 2003

(86) PCT No.: PCT/JP03/08579

§ 371 (c)(1),
(2), (4) Date: Dec. 1, 2004

(87) PCT Pub. No.: WO2004/006677

PCT Pub. Date: Jan. 22, 2004

(65) Prior Publication Data

US 2005/0176784 A1    Aug. 11, 2005

(30) Foreign Application Priority Data

Jul. 17, 2002  (JP)  ............................. 2002-208059

(51) Int. Cl.
*A01N 43/40* (2006.01)
*C07D 213/61* (2006.01)
(52) U.S. Cl. ...................... 514/357; 546/320
(58) Field of Classification Search ............. 514/357; 546/320
See application file for complete search history.

(56) References Cited

U.S. PATENT DOCUMENTS 2,957,007 A * 10/1960 McCall et al. ................ 549/8

FOREIGN PATENT DOCUMENTS

WO    02 089579    11/2002

OTHER PUBLICATIONS

Patent Abstracts of Japan, vol. 1998, No. 06, Apr. 30, 1998 & JP 10 029966 A (Mitsubishi Chem Corp.), Feb. 3, 1998.

* cited by examiner

*Primary Examiner*—Kamal A. Saeed

(57) ABSTRACT

The present invention relates to a novel malononitrile compound represented by the formula (I): wherein, $R^1$ represents a C1 to C5 (halo)alkyl and the like, $R^2$ represents a C1 to C5 (halo)alkyl, $R^3$ and $R^4$ are the same or different and are a C1 to C6 (halo)alkyl and the like, $R^5$ represents a halogen atom and the like, n is an integer of 0 to 4 and when n is 2 or more, $R^5$ may be the same or different. The malononitrile compound has an efficient pesticidal activity and can control effectively pests such as insect pests, acarine pests, nematode pests and the like

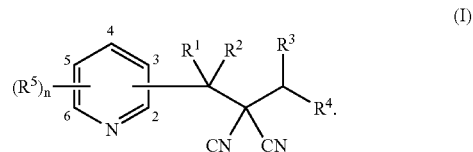

(I)

3 Claims, No Drawings

MALONONITRILE COMPOUNDS AND THEIR USE AS PESTICIDES

TECHNICAL FIELD

The present invention relates to malononitrile compounds and their use.

BACKGROUND ART

While various pesticide compositions have been used for the purpose of controlling pests such as insect pests, acarine pests, nematode pests and the like, sometimes the effect of those pesticide compositions is not always enough, and therefore the development of novel pesticide compositions having enough effect is desired.

It is an objective of the present invention to provide a method for controlling pests applying a novel compound having pesticidal activity and its effective dose to pests or their habitat.

DISCLOSURE OF INVENTION

The present inventors have intensively studied to find compounds having excellent pesticidal activity, and as a result, found out that the malononitrile compounds of formula (I) as depicted below have an excellent controlling activity for arthropod pests such as insect pests and acarine pests and pests such as nematode pests, thereby completing the present invention.

Namely, the present invention relates to a malononitrile compound represented by the formula (I) (hereinafter referred to as the present invention compound(s)):

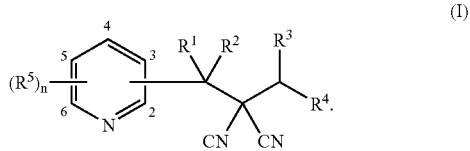

(I)

wherein, $R^1$ represents C1 to C5 (halo)alkyl, C2 to C5 (halo)alkenyl, C2 to C5 (halo)alkynyl or hydrogen atom, $R^2$ represents C1 to C5 (halo)alkyl, C1 to C5 (halo)alkyloxy, C2 to C5 (halo)alkenyl, C2 to C5 (halo)alkynyl, hydrogen atom or cyano, $R^3$ and $R^4$, which are the same or different, represent C1 to C6 (halo)alkyl, C2 to C6 (halo)alkenyl, C2 to C6 (halo)alkynyl, C3 to C6 (halo)cycloalkyl, C4 to C6 (halo)cycloalkenyl or hydrogen atom, or $R^3$ and $R^4$ together can represent C2 to C6 (halo)alkylene or C4 to C6 (halo)alkenylene, $R^5$ represents halogen atom, cyano, nitro, C1 to C4 (halo)alkyl, C2 to C4 (halo)alkenyl, C2 to C4 (halo)alkynyl, C1 to C4 (halo)alkyloxy, C1 to C4 (halo)alkylthio, C1 to C4 (halo)alkylsulfinyl, C1 to C4 (halo)alkylsulfonyl, C2 to C4 (halo)alkylcarbonyl, C2 to C4 (halo)alkyloxycarbonyl, C2 to C4 (halo)alkylcarbonyloxy, phenyloxy or phenylthio (the above-mentioned phenyloxy and phenylthio may be substituted with a halogen atom or a C1 to C3 alkyl), n is an integer of 0 to 4 and when n is 2 or more, $R^5$'s may be the same or different;

a pesticidal composition containing the present invention compound as active ingredient; and a method for controlling pests comprising applying an effective dose of the present invention compound to pests or habitat of pests.

MODE FOR CARRYING OUT THE INVENTION

In the present invention,

A (halo)alkyl means an alkyl whose 1 or more hydrogen atoms may be substituted with a halogen atom.

A (halo)alkyloxy means an alkyloxy whose 1 or more hydrogen atoms may be substituted with a halogen atom.

A (halo)alkenyl means an alkenyl whose 1 or more hydrogen atoms may be substituted with a halogen atom.

A (halo)alkynyl means an alkynyl whose 1 or more hydrogen atoms may be substituted with a halogen atom.

A (halo)cycloalkyl means a cycloalkyl whose 1 or more hydrogen atoms may be substituted with a halogen atom.

A (halo)cycloalkenyl means a cycloalkenyl whose 1 or more hydrogen atoms may be substituted with a halogen atom.

A (halo)alkylene means an alkylene whose 1 or more hydrogen atoms may be substituted with a halogen atom.

A (halo)alkenylene means an alkenylene whose 1 or more hydrogen atoms may be substituted with a halogen atom.

A (halo)alkylthio means an alkylthio whose 1 or more hydrogen atoms may be substituted with a halogen atom.

A (halo)alkylsulfinyl means an alkylsulfinyl whose 1 or more hydrogen atoms may be substituted with a halogen atom.

A (halo)alkylsulfonyl means an alkylsulfonyl whose 1 or more hydrogen atoms may be substituted with a halogen atom.

A (halo)alkylcarbonyl means an alkylcarbonyl whose 1 or more hydrogen atoms may be substituted with a halogen atom.

A (halo)alkyloxycarbonyl means an alkyloxycarbonyl whose 1 or more hydrogen atoms may be substituted with a halogen atom.

A (halo)alkylcarbonyloxy means an alkylcarbonyloxy whose 1 or more hydrogen atoms may be substituted with a halogen atom.

And the description of C1 to C6 and the like means the total number of carbon atoms constituting each substituents.

In the present invention compounds,

The C1 to C5 (halo)alkyl represented by $R^1$ includes, for example, methyl, ethyl, propyl, 1-methylethyl, 1,1-dimethylethyl, 2,2-dimethylpropyl, chloromethyl, fluoromethyl, difluoromethyl, trifluoromethyl, 2,2,2-trifluoroethyl and 1,1,2,2-tetrafluoroethyl.

The C2 to C5 (halo)alkenyl represented by $R^1$ includes, for example, vinyl, 2,2-difluorovinyl, 1,2,2-trifluorovinyl, 1-propenyl and 2-propenyl.

The C2 to C5 (halo)alkynyl represented by $R^1$ includes, for example, ethynyl, 1-propynyl, 2-propynyl and 3,3,3-trifluoro-1-propynyl.

The C1 to C5 (halo)alkyl represented by $R^2$ includes, for example, methyl, ethyl, propyl, 1-methylethyl, 1,1-dimethylethyl, 2,2-dimethylpropyl, chloromethyl, fluoromethyl, difluoromethyl, trifluoromethyl, 2,2,2-trifluoroethyl and 1,1,2,2-tetrafluoroethyl.

The C1 to C5 (halo)alkyloxy represented by $R^2$ includes, for example, methoxy, ethoxy, 1-methylethoxy, trifluoromethoxy, difluoromethoxy, 2,2,2-trifluoroethoxy and 1,1,2,2-tetrafluoroethoxy.

The C2 to C5 (halo)alkenyl represented by $R^2$ includes, for example, vinyl, 2,2-difluorovinyl, 1,2,2-trifluorovinyl, 1-propenyl and 2-propenyl.

The C2 to C5 (halo)alkynyl represented by $R^2$ includes, for example, ethynyl, 1-propynyl, 2-propynyl and 3,3,3-trifluoro-1-propynyl.

The C1 to C6 (halo)alkyl represented by $R^3$ or $R^4$ includes, for example, methyl, ethyl, 1-methylethyl, 2-methylpropyl, propyl, butyl, 3-methylbutyl, 3,3-chloromethyl, 2,2-difluoroethyl, 2,2-dichloroethyl, 3,3-difluoropropyl, 3,3-dichloropropyl, trifluoromethyl, trichloromethyl, 2,2,2-trifluoroethyl, 2,2,2-trichloroethyl, 3,3,3-trifluoropropyl, 3,3,3-trichloropropyl, 2,2-difluoropropyl, 3,3-difluorobutyl, pentafluoroethyl, 2,2,3,3,3-pentafluoropropyl, 1,1,2,2-tetrafluoroethyl and 2,2,3,3-tetrafluoropropyl.

The C2 to C6 (halo)alkenyl represented by $R^3$ or $R^4$ includes, for example, vinyl, allyl, 1-propenyl, 3-butenyl, 2-methyl-1-propenyl, 3-methyl-2-butenyl, 3-pentenyl, 4-pentenyl, 3-methyl-3-butenyl, 4-methyl-3-pentenyl, 1-chlorovinyl, 2-chlorovinyl, 1-fluorovinyl, 2-fluorovinyl, 2,2-dichlorovinyl, 2,2-dibromovinyl, 2,2-difluorovinyl, 1,2,2-trifluorovinyl, 1-(trifluoromethyl)vinyl, 2-chloro-2-propenyl, 3-chloro-2-propenyl, 2-fluoro-2-propenyl, 3-fluoro-2-propenyl, 3,3-dichloro-2-propenyl, 3,3-dibromo-2-propenyl, 3,3-difluoro-2-propenyl, 2,3,3-trifluoro-2-propenyl, 2-(trifluoromethyl)-2-propenyl, 2,3,3,3-tetrafluoro-1-propenyl, 1,2,3,3,3-pentafluoro-1-propenyl, 3,4,4-trifluoro-3-butenyl, 3,4,4,4-tetrafluoro-2-butenyl, 2,3,4,4,4-pentafluoro-2-butenyl and 4,5,5-trifluoro-4-pentenyl.

The C2 to C6 (halo)alkynyl represented by $R^3$ or $R^4$ includes, for example, ethynyl, 1-propynyl, 2-propynyl, 1-butynyl, 3-methyl-1-butynyl, 3,3-dimethyl-1-butynyl, 2-chloro-1-propynyl, 3-chloro-2-propynyl, 3,3,3-trifluoro-1-propynyl and 4,4,4-trifluoro-2-butynyl.

The C3 to C6 (halo)cycloalkyl includes, for example, cyclopropyl, 2,2-dichloro-1-cyclopropyl, 2,2-difluoro-1-cyclopropyl, 2,2,3,3-tetrafluoro-1-cyclopropyl, 2,2-dichloro-1-cyclobutyl, 2,2-difluoro-1-cyclobutyl, 2,2,3,3-tetrafluoro-1-cyclobutyl, cyclobutyl, cyclopentyl and cyclohexyl.

The C4 to C6 (halo)cycloalkenyl represented by $R^3$ or $R^4$ includes, for example, 2-fluoro-2-cyclopentenyl.

The C2 to C6 (halo)alkylene represented by $R^3$ and $R^4$ together includes, for example, ethylene, propylene, trimethylene and tetramethylene.

The C4 to C6 (halo)alkenylene represented by $R^3$ and $R^4$ includes, for example, 2-butenylene and 2-pentenylene.

The halogen atom represented by $R^5$ includes, for example, fluorine atom, chlorine atom and bromine atom.

The C1 to C4 (halo)alkyl represented by $R^5$ includes, for example, methyl, ethyl, propyl, 1-methylethyl, 1,1-dimethylethyl, trifluoromethyl, pentafluoroethyl, 2,2,2-trifluoroethyl and 1,1,2,2-tetrafluoroethyl.

The C2 to C4 (halo)alkenyl represented by $R^5$ includes, for example, vinyl, 1-propenyl, 2-propenyl and 2,2-difluorovinyl.

The C2 to C4 (halo)alkynyl represented by $R^5$ includes, for example, ethynyl, 1-propynyl, 2-propynyl and 3,3,3-trifluoro-1-propynyl.

The C1 to C4 (halo)alkyloxy represented by $R^5$ includes, for example, methoxy, ethoxy, propoxy, trifluoromethoxy, bromodifluoromethoxy, difluoromethoxy, chlorodifluoromethoxy, pentafluoroethoxy, 2,2,2-trifluoroethoxy and 1,1,2,2-tetrafluoroethoxy.

The C1 to C4 (halo)alkylthio represented by $R^5$ includes, for example, methylthio, trifluoromethylthio, 2,2,2-trifluoroethylthio and 1,1,2,2-tetrafluoroethylthio.

The C1 to C4 (halo)alkylsulfinyl represented by $R^5$ includes, for example, methylsulfinyl and trifluoromethylsulfinyl.

The C1 to C4 (halo)alkylsulfonyl represented by $R^5$ includes, for example, methylsulfonyl and trifluoromethylsulfonyl.

The C2 to C4 (halo)alkylcarbonyl represented by $R^5$ includes, for example, acetyl, propionyl and trifluoroacetyl.

The C2 to C4 (halo)alkyloxycarbonyl represented by $R^5$ includes, for example, methoxycarbonyl and 2,2,2-trifluoroethoxycarbonyl.

The C2 to C4 (halo)alkylcarbonyloxy represented by $R^5$ includes, for example, acetyloxy, propionyloxy and trifluoroacetyloxy.

The phenyloxy, which may be substituted with a halogen atom or a C1 to C3 alkyl, represented by $R^5$ includes, for example, phenoxy, p-methylphenoxy, m-methylphenoxy and p-chlorophenoxy.

The phenylthio, which may be substituted with a halogen atom or a C1 to C3 alkyl, represented by $R^5$ includes, for example, phenylthio, p-methylphenylthio, m-methylphenylthio and p-chlorophenylthio.

As the aspects of the present invention compound, for example, the following compounds are exemplified.

a malononitrile compound wherein $R^2$ is hydrogen atom in the formula (I);

a malononitrile compound wherein $R^2$ is methyl in the formula (I);

a malononitrile compound wherein $R^2$ is cyano in the formula (I);

a malononitrile compound wherein $R^1$ and $R^2$ are hydrogen atoms in the formula (I) in the formula (I);

a malononitrile compound wherein $R^1$ is hydrogen atom and $R^2$ is methyl in the formula (I);

a malononitrile compound wherein $R^1$ and $R^2$ are methyl in the formula (I);

a malononitrile compound wherein $R^4$ is hydrogen atom in the formula (I);

a malononitrile compound wherein $R^4$ is a C2 to C6 alkenyl in the formula (I);

a malononitrile compound wherein $R^4$ is vinyl in the formula (I);

a malononitrile compound wherein $R^4$ is 2-propenyl in the formula (I);

a malononitrile compound wherein $R^4$ is 2-methyl-1-propenyl in the formula (I);

a malononitrile compound wherein $R^4$ is a C2 to C6 haloalkenyl in the formula (I);

a malononitrile compound wherein $R^4$ is 2,2-difluorovinyl in the formula (I);

a malononitrile compound wherein $R^4$ is 1-(trifluoromethyl)vinyl in the formula (I);

a malononitrile compound wherein $R^4$ is 3,3-difluoro-2-propenyl in the formula (I);

a malononitrile compound wherein $R^4$ is 2,3,3-trifluoro-2-propenyl in the formula (I);

a malononitrile compound wherein $R^4$ is 3,3,3-trifluoro-1-propenyl in the formula (I);

a malononitrile compound wherein $R^4$ is a C2 to C6 haloalkynyl in the formula (I);

a malononitrile compound wherein $R^4$ is a C1 to C6 fluoroalkyl in the formula (I);

a malononitrile compound wherein $R^4$ is fluoromethyl in the formula (I);

a malononitrile compound wherein $R^4$ is 2,2-difluoroethyl in the formula (I);

a malononitrile compound wherein $R^4$ is 2,2,2-trifluoroethyl in the formula (I);

a malononitrile compound wherein $R^4$ is pentafluoroethyl in the formula (I);

a malononitrile compound wherein $R^4$ is 3,3,3-trifluoropropyl in the formula (I);

a malononitrile compound wherein $R^4$ is 2,2,3,3,3-pentafluoropropyl in the formula (I);

a malononitrile compound wherein $R^4$ is a C3 to C6 cycloalkyl in the formula (I);

a malononitrile compound wherein $R^4$ is 2,2-dichlorocyclopropyl in the formula (I);

a malononitrile compound wherein $R^4$ is cyclopropyl in the formula (I);

a malononitrile compound wherein $R^4$ is cyclobutyl in the formula (I);

a malononitrile compound wherein $R^3$ is hydrogen atom and $R^4$ is a C2 to C6 alkenyl in the formula (I);

a malononitrile compound wherein $R^3$ is hydrogen atom and $R^4$ is vinyl, 2-propenyl or 2-methyl-1-propenyl in the formula (I);

a malononitrile compound wherein $R^3$ is hydrogen atom and $R^4$ is a C2 to C6 haloalkenyl in the formula (I);

a malononitrile compound wherein $R^3$ is hydrogen atom and $R^4$ is 2,2-difluorovinyl, 1-(trifluoromethyl)vinyl, 3,3-difluoro-2-propenyl, 2,3,3-trifluoro-2-propenyl or 3,3,3-trifluoro-1-propenyl in the formula (I);

a malononitrile compound wherein $R^3$ is hydrogen atom and $R^4$ is a C1 to C6 haloalkyl in the formula (I);

a malononitrile compound wherein $R^3$ is hydrogen atom and $R_4$ is fluoromethyl, 2,2-difluoroethyl, 2,2,2-trifluoroethyl, 1,1,2,2,2-pentafluoroethyl, 3,3,3-trifluoropropyl or 2,2,3,3,3-pentafluoropropyl in the formula (I);

a malononitrile compound wherein $R^3$ is hydrogen atom and $R^4$ is a C3 to C6 (halo)cycloalkyl in the formula (I);

a malononitrile compound wherein $R^3$ is hydrogen atom and $R^4$ is cyclopropyl, cyclobutyl or 2,2-dichlorocyclopropyl in the formula (I);

a malononitrile compound wherein $R^1$, $R^2$ and $R^3$ are hydrogen atoms and $R^4$ is vinyl, 2-propenyl or 2-methyl-2-propenyl in the formula (I);

a malononitrile compound wherein $R^1$, $R^2$ and $R^3$ are (trifluoromethyl)vinyl, hydrogen atoms and $R^4$ is 2,2-difluorovinyl, 1-3,3-difluoro-2-propenyl, 2,3,3-trifluoro-2-propenyl or 3,3,3-trifluoro-1-propenyl in the formula (I);

a malononitrile compound wherein $R^1$ and $R^2$ are methyl, and $R^3$ is hydrogen atom and $R^4$ is 2,2-difluorovinyl, 1-(trifluoromethyl)vinyl, 3,3-difluoro-2-propenyl, 2,3,3-trifluoro-2-propenyl or 3,3,3-trifluoro-1-propenyl in the formula (I);

a malononitrile compound wherein $R^1$ and $R^3$ are hydrogen atoms, and $R^2$ is methyl and $R^4$ is 2,2-difluorovinyl, 1-(trifluoromethyl)vinyl, 3,3-difluoro-2-propenyl, 2,3,3-trifluoro-2-propenyl or 3,3,3-trifluoro-1-propenyl in the formula (I);

a malononitrile compound wherein $R^1$, $R^2$ and $R^3$ are hydrogen atoms and $R^4$ is fluoromethyl, 2,2-difluoroethyl, 2,2,2-trifluoroethyl, pentafluoroethyl, 3,3,3-trifluoropropyl or 2,2,3,3,3-pentafluoropropyl in the formula (I);

a malononitrile compound wherein $R^1$ and $R^3$ are hydrogen atoms, and $R^2$ is methyl and $R^4$ is fluoromethyl, 2,2-difluoroethyl, 2,2,2-trifluoroethyl, pentafluoroethyl, 3,3,3-trifluoropropyl or 2,2,3,3,3-pentafluoropropyl in the formula (I);

a malononitrile compound wherein $R^1$ and $R^2$ are methyl, and $R^3$ is hydrogen atom and $R^4$ is fluoromethyl, 2,2-difluoroethyl, 2,2,2-trifluoroethyl, pentafluoroethyl, 3,3,3-trifluoropropyl or 2,2,3,3,3-pentafluoropropyl in the formula (I);

a malononitrile compound wherein $R^1$, $R^2$ and $R^3$ are hydrogen atoms and $R^4$ is cyclopropyl, cyclobutyl or 2,2-dichlorocyclopropyl in the formula (I);

a malononitrile compound wherein n is 0 in the formula (I);

a malononitrile compound wherein n is 1 and $R^5$ is 1,1-dimethylethyl in the formula (I);

a malononitrile compound wherein n is 1 and $R^5$ is trifluoromethyl in the formula (I);

a malononitrile compound wherein n is 1 and $R^5$ is cyano in the formula (I);

a malononitrile compound wherein n is 1 and $R^5$ is nitro in the formula (I);

a malononitrile compound wherein n is 1 and $R^5$ is bromine atom in the formula (I);

a malononitrile compound wherein n is 1 and $R^5$ is chlorine atom in the formula (I);

a malononitrile compound wherein n is 2 and $R^5$'s are chlorine atoms in the formula (I);

a malononitrile compound wherein n is 1 and $R^5$ is fluorine atom in the formula (I);

a malononitrile compound wherein n is 2 and $R^5$'s are fluorine atoms in the formula (I);

a malononitrile compound wherein the carbon atom binding to $R^1$ and $R^2$ is bound to pyridine ring at 2-position in the formula (I);

a malononitrile compound wherein the carbon atom binding to $R^1$ and $R^2$ is bound to pyridine ring at 3-position in the formula (I);

a malononitrile compound wherein the carbon atom binding to $R^1$ and $R^2$ is bound to pyridine ring at 4-position in the formula (I).

The following will describe a production process for the present invention compounds.

The present invention compounds can be produced, for example, according to the following (Production Process 1) to (Production Process 5).

(Production Process 1)

A process wherein compound (a) is reacted with compound (b):

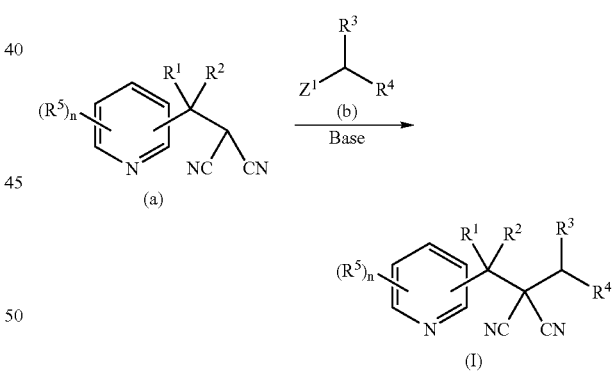

wherein, $R^1$, $R^2$, $R^3$, $R^4$, $R^5$ and n are as defined above and $Z^1$ represents a halogen atom, methanesulfonyl, trifluoromethanesulfonyl or toluenesulfonyl.

The reaction is generally carried out in the presence of base in a solvent.

The solvent to be used in the reaction includes, for example, acid amides such as N,N-dimethylformamide and the like, ethers such as diethyl ether, tetrahydrofuran and the like, organic sulfurs such as dimethylsulfoxide, sulfolane and the like, halogenated hydrocarbons such as 1,2-dichloroethane, chlorobenzene and the like, aromatic hydrocarbons such as toluene, xylene and the like, and mixtures thereof.

The base to be used in the reaction includes, for example, inorganic bases such as sodium hydride, sodium carbonate, potassium carbonate and the like, alkali metal alkoxides such as potassium t-butoxide and the like, alkali metal amides such as lithium diisopropylamide and the like, and organic bases such as dimethylaminopyridine, 1,4-diazabicyclo[2.2.2]octane, 1,8-diazabicyclo[5.4.0]-7-undecene and the like. The amount of the base that can be used in the reaction is usually 1 to 10 moles relative to 1 mole of compound (a).

The amount of compound (b) to be used in the reaction is usually 1 to 10 moles relative to 1 mole of compound (a).

The reaction temperature is usually in the range of −20° C. to 100° C., and the reaction time is usually in the range of 1 to 24 hours.

After completion of the reaction, the present invention compound represented by the formula (I) can be isolated by subjecting the reaction mixture to ordinary post-treatment such as adding the reaction mixture into water, extracting with an organic solvent, concentrating the extract and the like. The isolated present invention compound represented by the formula (I) can be purified by a technique such as chromatography, recrystallization and the like, if necessary.

(Production Process 2)

A process wherein compound (c) is reacted with compound (d):

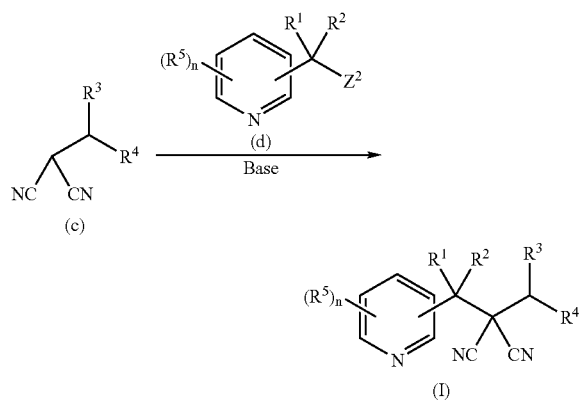

wherein, $R^1$, $R^2$, $R^3$, $R^4$, $R^5$ and n are as defined above and $Z^2$ represents a halogen atom, methanesulfonyl, trifluoromethanesulfonyl or toluenesulfonyl.

The reaction is generally carried out in the presence of base in a solvent.

The solvent to be used in the reaction includes, for example, acid amides such as N,N-dimethylformamide and the like, ethers such as diethyl ether, tetrahydrofuran and the like, organic sulfurs such as dimethylsulfoxide, sulfolane and the like, halogenated hydrocarbons such as 1,2-dichloroethane, chlorobenzene and the like, aromatic hydrocarbons such as toluene, xylene and the like, and mixtures thereof.

The base to be used in the reaction includes, for example, inorganic bases such as sodium hydride, sodium carbonate, potassium carbonate and the like, alkali metal alkoxides such as potassium t-butoxide and the like, alkali metal amides such as lithium diisopropylamide and the like, and organic bases such as 4-dimethylaminopyridine, 1,4-diazabicyclo[2.2.2]octane, 1,8-diazabicyclo[5.4.0]-7-undecene and the like. The amount of the base that can be used in the reaction is usually 1 to 10 moles relative to 1 mole of compound (c).

The amount of compound (d) to be used in the reaction is usually 1 to 10 moles relative to 1 mole of compound (c).

The reaction temperature is usually in the range of −20° C. to 100° C., and the reaction time is usually in the range of 1 to 24 hours.

After completion of the reaction, the present invention compound represented by the formula (I) can be isolated by subjecting the reaction mixture to ordinary post-treatment such as adding the reaction mixture into water, extracting with an organic solvent, concentrating the extract and the like. The isolated present invention compound represented by the formula (I) can be purified by a technique such as chromatography, recrystallization and the like, if necessary.

The compound (a) can be produced, for example, according to the route represented by the following scheme:

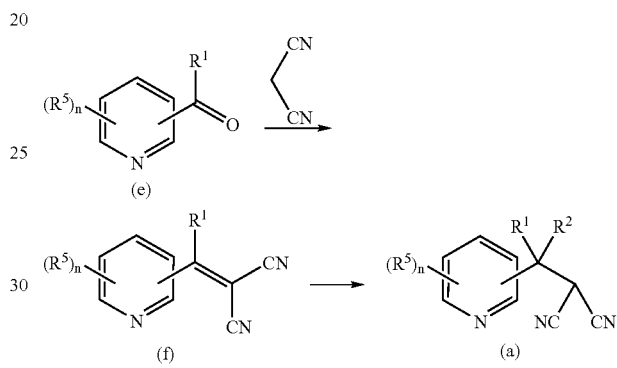

wherein, $R^1$, $R^2$, $R^5$ and n are as defined above.

(Step 1)

The compound (f) can be produced by reacting compound (e) with malononitrile.

The reaction is generally carried out in the presence of base in a solvent. The solvent to be used in the reaction includes, for example, acid amides such as N,N-dimethylformamide and the like, ethers such as diethyl ether, tetrahydrofuran and the like, halogenated hydrocarbons such as chloroform, 1,2-dichloroethane, chlorobenzene and the like, aromatic hydrocarbons such as toluene, xylene and the like, alcohols such as methanol, ethanol, isopropyl alcohol and the like, and mixtures thereof.

The base to be used in the reaction includes, for example, tetrabutylammonium hydroxide. The amount of the base that can be used in the reaction is usually 0.01 to 0.5 moles relative to 1 mole of compound (e).

The amount of malononitrile to be used in the reaction is usually 1 to 10 moles relative to 1 mole of compound (e).

The reaction temperature is usually in the range of −20° C. to 200° C., and the reaction time is usually in the range of 1 to 24 hours.

The reaction may be carried out with removing the water formed by the reaction from the reaction system, if necessary.

After completion of the reaction, the compound (f) can be isolated by subjecting the reaction mixture to ordinary post-treatment such as adding the reaction mixture into water, extracting with an organic solvent, concentrating the extract and the like. The isolated compound (f) can be purified by a technique such as chromatography, recrystallization and the like, if necessary.

(Step 2)

(1) In the Case where $R^2$ Represents a C1 to C5 alkyl, a C2 to C5 alkenyl or a C2 to C5 alkynyl The compound (a) can be produced by reacting compound (f) with an organometallic compound which corresponds to $R^2$.

The reaction is generally carried out in a solvent, and if necessary, in the presence of a copper salt.

The solvent to be used in the reaction includes, for example, ethers such as diethyl ether, tetrahydrofuran and the like, aromatic hydrocarbons such as toluene, xylene and the like, and mixtures thereof.

The organometallic compound to be used in the reaction includes, for example, organomagnesium compounds such as methylmagnesium iodide, ethylmagnesium bromide, isopropylmagnesium bromide, vinylmagnesium bromide, ethynylmagnesium bromide, dimethylmagnesium and the like, organolithium compounds such as methyllithium and the like, organozinc compounds such as diethylzinc and the like, and organocopper compounds such as trifluoromethylcopper and the like. The amount of the organometallic compound that can be used in the reaction is usually 1 to 10 moles relative to 1 mole of compound (f).

The copper salt to be used in the reaction includes, for example, cuprous(I) iodide, cuprous(I) bromide and the like. The amount of the copper salt to be used in the reaction is usually not more than 1 mole relative to 1 mole of compound (f).

The reaction temperature is usually in the range of $-20°$ C. to $100°$ C., and the reaction time is usually in the range of 1 to 24 hours.

After completion of the reaction, the compound (a) can be isolated by subjecting the reaction mixture to ordinary post-treatment such as adding the reaction mixture into water, extracting with an organic solvent, concentrating the extract and the like. The isolated compound (a) can be purified by a technique such as chromatography, recrystallization and the like, if necessary.

(2) In the Case where $R^2$ Represents a Hydrogen Atom

The compound (a) can be produced by reacting compound (f) with a reductant.

The reaction is usually carried out in a solvent.

The solvent to be used in the reaction includes, for example, ethers such as diethyl ether, tetrahydrofuran and the like, aromatic hydrocarbons such as toluene, xylene and the like, alcohols such as methanol, ethanol, propanol and the like, water and mixtures thereof.

The reductant to be used in the reaction includes, for example, sodium borohydride. The amount of the reductant to be used in the reaction is usually 0.25 to 2 moles relative to 1 mole of compound (f).

The reaction temperature is usually in the range of $0°$ C. to $50°$ C., and the reaction time is usually in the range of sec to 24 hours.

After completion of the reaction, the compound (a) can be isolated by subjecting the reaction mixture to ordinary post-treatment such as adding the reaction mixture into water, extracting with an organic solvent, concentrating the extract and the like. The isolated compound (a) can be purified by a technique such as chromatography, recrystallization and the like, if necessary.

(3) In the Case Where $R^2$ Represents a Cyano

The compound (a) can be produced by reacting compound (f) with a cyanide.

The reaction is usually carried out in a solvent.

The solvent to be used in the reaction includes, for example, ethers such as diethyl ether, tetrahydrofuran and the like, aromatic hydrocarbons such as toluene, xylene and the like, and mixtures thereof.

The cyanide to be used in the reaction includes, for example, tetrabutylammonium cyanide. The amount of the cyanide to be used in the reaction is usually 1 to 10 moles relative to 1 mole of compound (f).

The reaction temperature is usually in the range of $-20°$ C. to $100°$ C., and the reaction time is usually in the range of 1 to 24 hours.

After completion of the reaction, the compound (a) can be isolated by subjecting the reaction mixture to ordinary post-treatment such as adding the reaction mixture into water, extracting with an organic solvent, concentrating the extract and the like. The isolated compound (a) can be purified by a technique such as chromatography, recrystallization and the like, if necessary.

(Production Process 3)

Among the present invention compounds, the compound wherein $R^2$ is a C1 to C5 (halo)alkyl, $R^1$ and $R^3$ are hydrogen atoms and $R^4$ is a vinyl, can be also produced according to the following method.

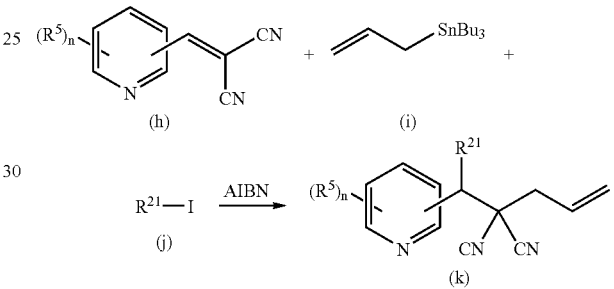

wherein, $R^5$ and n are as defined above, $R^{21}$ represents a C1 to C5 (halo)alkyl, Bu is butyl and AIBN is azobisisobutyronitrile.

The reaction can be carried out according to the method described in J. Am. Chem. Soc., 110, 1289 (1988).

(Production Process 4)

Among the present invention compounds, the compound wherein $R^2$ is cyano, $R^1$ and $R^3$ are hydrogen atoms and $R^4$ is a vinyl, can be also produced according to the following method.

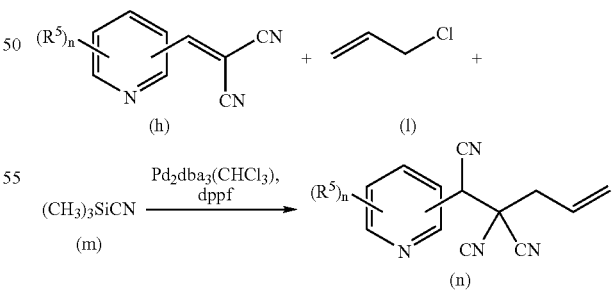

wherein, $R^5$ and n are as defined above, dba is dibenzylideneacetone and dppf is 1,1'-bis(diphenylphosphino)ferrocene.

The reaction can be carried out according to the similar condition described in Tetrahedron Lett., 41, 2911 (2000).

(Production Process 5)

Among the present invention compounds, the compound wherein $R^2$ is a C1 to C5 (halo)alkyloxy, $R^1$ and $R^3$ are hydrogen atoms and $R^4$ is a vinyl, can be also produced according to the following method.

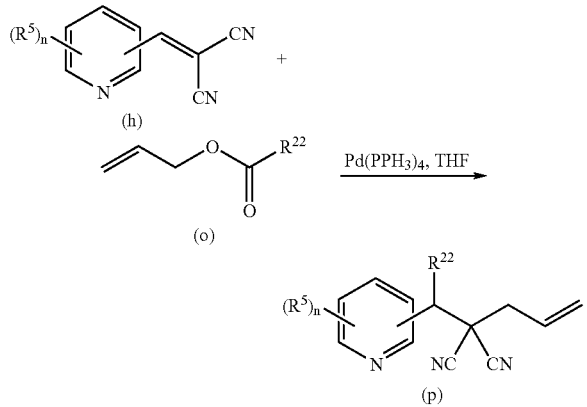

wherein, $R^5$ and n are as defined above, $R^{22}$ represents a C1 to C5 (halo)alkyloxy, Ph is phenyl and THF is tetrahydrofuran.

The reaction can be carried out according to the similar condition described in J. Am. Chem. Soc., 120, 6838 (1998).

The pests against which the present invention compound has control activity may include, for example, arthropods such as insect pests and acarine pests and the like, and nematode pests. Specific examples are listed below:

Hemiptera:
  Delphacidae such as *Laodelphax striatellus, Nilaparvata lugens, Sogatella furcifera* and the like,
  Deltocephalidae such as *Nephotettix cincticeps, Nephotettix virescens* and the like,
  Aphididae such as *Aphis gossypii, Myzus persicae* and the like,
  Pentatomidae such as *Nezara antennata, Riptortus clavetus, Eysarcoris lewisi, Eysarcoris parvus, Plautia stali, Halyomorpha mista* and the like,
  Aleyrodidae such as *Trialeurodes vaporariorum, Bemisia argentifolii* and the like,
  Coccidae such as *Aonidiella aurantii, Comstockaspis perniciosa, Unaspis citri, Ceroplastes rubens, Icerya purchasi* and the like,
  Tingidae,
  Psyllidae, and the like;
Lepidoptera:
  Pyralidae such as *Chilo suppressalis, Cnaphalocrocis medinalis, Notarcha derogata, Plodia interpunctella* and the like,
  Noctuidae such as *Spodoptera litura, Pseudaletia separata, Thoricoplusia* spp., *Heliothis* spp., *Helicoverpa* spp. and the like,
  Pieridae such as *Pieris rapae* and the like,
  Tortricidae such as *Adoxophyes* spp., *Grapholita molesta, Cydia pomonella* and the like,
  Carposinidae such as *Carposina niponensis* and the like,
  Lyonetiidae such as *Lyonetia* spp. and the like,
  Lymantriidae such as *Lymantria* spp., *Euproctis* spp., and the like,
  Yponomeutidae such as *Plutella xylostella* and the like,
  Gelechiidae such as *Pectinophora gossypiella* and the like,
  Arctiidae such as *Hyphantria cunea* and the like,
  Tineidae such as *Tinea translucens, Tineola bisselliella* and the like;
Diptera:
  Calicidae such as *Culex pipiens pallens, Culex tritaeniorhynchus, Culex quinquefasciatus* and the like,
  Aedes spp. such as *Aedes aegypti, Aedes albopictus* and the like,
  Anopheles spp. such as *Anopheles sinensis* and the like,
  Chironomidae,
  Muscidae such as *Musca domestica, Muscina stabulans* and the like,
  Calliphoridae,
  Sarcophagidae,
  Fanniidae,
  Anthomyiidae such as *Delia platura, Delia antiqua* and the like,
  Tephritidae,
  Drosophilidae,
  Psychodidae,
  Tabanidae,
  Simuliidae,
  Stomoxyidae,
  Agromyzidae, and the like;
Coleoptera:
  Diabrotica spp. such as *Diabrotica virgifera virgifera, Diabrotica undecimpunctata howardi* and the like,
  Scarabaeidae such as *Anomala cuprea, Anomala rufocuprea* and the like,
  Curculionidae such as *Sitophilus zeamais, Lissorhoptrus oryzophilus, Callosobruchuys chienensis* and the like,
  Tenebrionidae such as *Tenebrio molitor, Tribolium castaneum* and the like,
  Chrysomelidae such as *Oulema oryzae, Aulacophora femoralis, Phyllotreta striolata, Leptinotarsa decemlineata* and the like,
  Anobiidae,
  Epilachna spp. such as *Epilachna vigintioctopunctata* and the like,
  Lyctidae,
  Bostrychidae,
  Cerambycidae,
  Paederus fuscipes;
Blattodea: *Blattella germanica, Periplaneta fuliginosa, Periplaneta americana, Periplaneta brunnea, Blatta orientalis* and the like;
Thysanoptera: *Thrips palmi, Thrips tabaci, Frankliniella occidentalis, Frankliniella intonsa* and the like;
Hymenoptera: Formicidae, Vespidae, bethylid wasp, Tenthredinidae such as *Athalia japonica*, and the like;
Orthoptera: Gryllotalpidae, Acrididae, and the like;
Aphaniptera: *Ctenocephalides felis, Ctenocephalides canis, Pulex irritans, Xenopsylla cheopis*, and the like;
Anoplura: *Pediculus humanus corporis, Phthirus pubis, Haematopinus eurysternus, Dalmalinia ovis*, and the like;
Isoptera: *Reticulitermes speratus, Coptotermes formosanus*, and the like;
Acarina:
  Tetranychidae such as *Tetranychus urticae, Tetranychus kanzawai, Panonychus citri, Panonychus ulmi, Oligonychus* spp., and the like,
  Eriophyidae such as *Aculops pelekassi, Aculus schlechtendali*, and the like,
  Tarsonemidae such as *Polyphagotarsonemus latus*, and the like,
  Tenuipalpidae,
  Tuckerellidae, Ixodidae such as *Haemaphysalis longicornis, Haemaphysalis flava, Dermacentor taiwanicus, Ixodes ovatus, Ixodes persulcatus, Boophilus microplus*, and the like, Acaridae such as *Tyrophagus putrescentiae*, and the like, Epidermoptidae such as *Dermatophagoides farinae, Dermatophagoides ptrenyssnus*, and the like, Cheyletidae such as *Cheyletus eruditus, Cheyletus malaccensis, Cheyletus moorei*, and the like, Dermanyssidae;

Araneae: *Chiracanthium japonicum, Latrodectus hasseltii*, and the like;

Chilopoda: *Thereuonema hilgendorfi, Scolopendra subspinipes*, and the like;

Diplopoda: *Oxidus gracilis, Nedyopus tambanus*, and the like;

Isopoda: *Armadillidium vulgare*, and the like;

Gastropoda: *Limax marginatus, Limax flavus*, and the like;

Nematoda: *Pratylenchus coffeae, Pratylenchus fallax, Heterodera glycines, Globodera rostochiensis, Meloidogyne hapla, Meloidogyne incognita*, and the like.

The pesticide composition of the present invention contains the present invention compound and an inert carrier. Generally, it is a preparation obtained by mixing the present invention compound and a carrier such as a solid carrier, a liquid carrier and a gaseous carrier, and if necessary, adding a surfactant and other adjuvant for formulation. The formulation includes, for example, an emulsion, an oil solution, a shampoo formulation, a flowable formulation, a powder, a wettable powder, a granule, a paste formulation, a microcapsule, a foam, an aerosol, a carbon dioxide gas formulation, a tablet, a resin formulation and the like. These formulations can be converted to use into a poison bait, a pyrethrum coil, an electric mosquito mat, a smoking agent, a fumigant or sheet.

In the pesticide composition of the present invention, the present invention compound is usually contained in an amount of 0.1% to 95% by weight.

The solid carrier for formulation includes, for example, a fine power and a granule of clays (e.g., kaolin clay, diatomite, bentonite, Fubasami clay, acid clay, etc.), synthetic hydrated silicon oxide, talc, ceramic, other inorganic minerals (e.g., sericite, quartz, sulfur, activated carbon, calcium carbonate, hydrated silica) or chemical fertilizers (e.g., ammonium sulfate, ammonium phosphate, ammonium nitrate, ammonium chloride, urea).

The liquid carrier for formulation includes, for example, aromatic or aliphatic hydrocarbons (e.g., xylene, toluene, alkylnaphthalene, phenylxylylethane, kerosine, light oil, hexane, cyclohexane), halogenated hydrocarbons (e.g., chlorobenzene, dichloromethane, dichloroethane, trichloroethane), alcohols (e.g., methanol, ethanol, isopropyl alcohol, butanol, hexanol, ethylene glycol), ethers (e.g., diethyl ether, ethylene glycol dimethyl ether, diethylene glycol monomethyl ether, diethylene glycol monoethyl ether, propylene glycol monomethyl ether, tetrahydrofuran, dioxane), esters (e.g., ethyl acetate, butyl acetate), ketones (e.g., acetone, methyl ethyl ketone, methyl isobutyl ketone, cyclohexanone), nitriles (e.g., acetonitrile, isobutyronitrile), sulfoxides (e.g., dimethylsulfoxide), acid amides (e.g., N,N-dimethylformamide, N,N-dimethylacetamide), vegetable oils (e.g., soy bean oil, cotton seed oil), vegetable essential oils (e.g., orange oil, hyssop oil, lemon oil) and water.

The gaseous carrier for formulation includes, for example, butane gas, chlorofluorocarbons, liquefied petroleum gas (LPG), dimethyl ether, carbon dioxide and the like.

The surfactant for formulation includes, for example, alkyl sulfate salts, alkylsulfonic acid salts, alkylarylsulfonic acid salts, alkyl aryl ethers and their polyoxyethylene derivatives, polyethylene glycol ethers, polyhydric alcohol esters, and sugar alcohol derivatives.

The other adjuvant for formulation includes, for example, binders, dispersants and stabilizers, and specifically for example, casein, gelatin, polysaccharides (e.g., starch, gum arabic, cellulose derivatives, alginic acid), lignin derivatives, bentonite, sugars, synthetic water-soluble polymers (e.g., polyvinyl alcohol, polyvinylpyrrolidone, polyacrylic acid), PAP (isopropyl acid phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids, and fatty acid esters.

The base for resin formulation includes, for example, polyvinyl chloride, polyurethane and the like. To these bases, if necessary, a plasticizer such as phthalate (e.g., dimethyl phthalate, dioctyl phthalate), adipate and stearate may be added. The resin formulation can be obtained by kneading the compound into the base using a known kneader and then formulating by injection molding, extrusion molding, press molding and the like, and further, if necessary, via a process for molding, cutting and the like, the resin formulation can be converted into a resin preparation such as board, film, tape, net, string and the like. These resin preparations can be converted into, for example, an animal collar, an animal ear tag, a sheet preparation, an attraction string, a gardening stick.

A base for the poison bait includes, for example, grain powders, vegetable oils, sugars, and crystalline cellulose, and further, if necessary, antioxidants such as dibutylhydroxytoluene and nordihydroguaiaretic acid, preservatives such as dehydroacetic acid, agents for preventing children and pets from erroneously eating such as hot pepper powder, and pest-attractive flavors such as cheese flavor, onion flavor and peanut oil may be added to the base.

Pests can be controlled by applying an effective dose of the present invention compound to pests directly and/or habitats of pests (e.g., plant, animal, soil). Usually the preparation of the pesticide composition of the present invention is used as the present invention compound.

When the pesticide composition of the present invention is used for a control of pests in agriculture and forestry, the application amount is usually 1 to 10,000 g/ha, preferably 10 to 1,000 g/ha, as an active ingredient. The emulsions, wettable powders, flowables, and microcapsule formulations are usually applied after dilution with water to have an active ingredient concentration of 1 to 10,000 ppm, while powders and granules are usually applied as such. These preparations may be sprayed directly to the plant to be protected from pests. The pests living in a soil can be controlled by treating the soil with these preparations, and the preparations can also be applied to treat seedbeds prior to the planting plants or to treat planting holes or plant bottoms in the planting. Furthermore, the sheet preparation of the pesticide composition of the present invention can be applied by a method such as winding around plants, stretching in the vicinity of plants and laying on the soil surface at the plant bottom.

When the pesticide composition of the present invention is used for a control of epidemic, the application amount is usually 0.001 to 10 mg/m$^3$ as an active ingredient in case of application for open space, and 0.001 to 100 mg/m$^2$ as an active ingredient in case of application for plane surface. The emulsions, wettable powders, flowables, and microcapsule formulations are usually applied after dilution with water to have an active ingredient concentration of 0.01 to 10,000 ppm, while oil solutions, aerosols, smoking agents and poison baits are usually applied as such.

When the pesticide composition of the present invention is used for a control of parasite living outside of a livestock such as caw, horse, pig, sheep, goat and chicken, and a small animal such as dog, cat, rat and mouse, the pesticide composition can be applied to said animal by a veterinarily known method. Specifically, for systemic control, the pesticide composition is administered by means of, for example, a tablet, a mixture with feed, a suppository or an injection (e.g., intramuscular, subcutaneous, intravenous, intraperitoneal), and for non-systemic control, it is applied by a method such as spraying an oil solution or an aqueous liquid formulation, carrying out pour-on treatment or spot-on treatment, washing said animal with a shampoo formulation, attaching the resin formulation on said animal as a collar or an ear-tag, and the like. When the present invention compound is administered to an animal, its amount is usually in the range of 0.1 to 1,000 mg/kg body weight of the animal.

The pesticide composition of the present invention can also be used in admixture or combination with other insecticides, nematocides, acaricides, fungicides, herbicides, plant growth regulators, synergists, fertilizers, soil conditioners, animal feeds, and the like.

The active ingredients of such other insecticide and acaricide include, for example, pyrethroid compounds such as allethrin, tetramethrin, prallethrin, phenothrin, resmethrin, cyphenothrin, permethrin, cypermethrin, alpha-cypermethrin, zeta-cypermethrin, deltamethrin, tralomethrin, cyfluthrin, beta-cyfluthrin, cyhalothrin, lambda-cyhalothrin, flumethrin, imiprothrin, etofenprox, fenvalerate, esfenvalerate, fenpropathrin, silafluofen, bifenthrin, transfluthrin, flucythrinate, tau-fluvalinate, acrinathrin and tefluthrin; organophosphorus compounds such as dichlorvos, fenitrothion, cyanophos, profenofos, sulprofos, phenthoate, isoxathion, tetrachlorvinphos, fenthion, chlorpyriphos, diazinon, acephate, terbufos, phorate, chlorethoxyfos, fosthiazate, ethoprophos, cadusafos and methidathion; carbamate compounds such as propoxur, carbaryl, metoxadiazone, fenobucarb, methomyl, thiodicarb, alanycarb, benfuracarb, oxamyl, aldicarb and methiocarb; benzoylphenylurea compounds such as luf enuron, chlorfluazuron, hexaflumuron, diflubenzuron, triflumuron, teflubenzuron, flufenoxuron, fluazuron, novaluron and triazuron; juvenile hormone-like substances such as pyriproxyfen, methoprene, hydroprene and fenoxycarb; neonicotinoid compounds such as acetamiprid, nitenpyram, thiacloprid, thiamethoxam and dinotefuran; N-phenyl-pyrazole compounds such as acetoprole and ethiprole; benzoylhydrazine compounds such as tebufenozide, chromafenozide, methoxyfenozide and halofenozide; diafenthiuron; pymetrozine; flonicamid; triazamate; buprofezin; spinosad; emamectin benzoate; chlorfenapyr; indoxacarb MP; pyridalyl; cyromazine; fenpyroximate; tebufenpyrad; tolfenpyrad; pyridaben; pyrimidifen; fluacrypyrim; etoxazole; fenazaquin; acequinocyl; hexythiazox; clofentezine; fenbutatin oxide; dicofol, propargite; abamectin; milbemectin; amitraz; cartap; bensultap; thiocyclam; endosulfan; spirodiclofen; spiromesifen; and azadirachtin.

The active ingredients of such other fungicide include, for example, strobilurin compounds such as azoxystrobin; organophosphorus compounds such as tolclofos-methyl; azole compounds such as triflumizole, pefurazoate and difenoconazole; fthalide; flutolanil; validamycin; probenazole; diclomezine; pencycuron; dazomet; kasugamycin; IBP; pyroquilon; oxolinic acid; tricyclazole; ferimzone; mepronil; EDDP; isoprothiolane; carpropamid; diclocymet; furametpyr; fludioxonil; procymidone; and diethofencarb.

The present invention will be further illustrated by the following production examples, formulation examples, and test examples; however, the present invention is not limited to these examples. First, production examples of the present invention compounds are exemplified.

PRODUCTION EXAMPLE 1

((6-Chloro-3-pyridyl)methyl)malononitrile (58 mg) was dissolved in N,N-dimethylformamide (2 ml), and sodium hydride (60% in oil, 14 mg) was added to the solution with stirring under ice-cooling. Then allyl bromide (0.13 ml) was added dropwise thereto, and the mixture was stirred overnight at room temperature. To the reaction mixture was added 10% hydrochloric acid, and extracted with diethyl ether. The organic layer was washed successively with 10% hydrochloric acid and saturated brine, dried over anhydrous magnesium sulfate and concentrated under reduced pressure. The residue obtained was subjected to silica gel column chromatography to give 26 mg of 2-allyl-2-((6-Chloro-3-pyridyl)methyl)malononitrile represented by the following formula (hereinafter referred to as the present invention compound (1)).

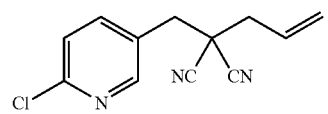

Yield 37%

$n_D^{22.5}$ 1.5380

PRODUCTION EXAMPLE 2

To tetrahydrofuran (13 ml) were added ((6-Chloro-3-pyridyl)methylidene)malononitrile (0.50 g), tris(dibenzylideneacetone)dipalladium chloroform complex (70 mg) and 1,1'-bis(diphenylphosphino)ferrocene (0.15 g) under nitrogen atmosphere, and then allyl chloride (0.41 g) and trimethylsilylcyanide (0.53 g) were added thereto. The solution was stirred at 75° C. for a day. Then the reaction mixture was filtered through silica gel, and concentrated. The residue was subjected to silica gel column chromatography to give 0.48 g of 1-(6-Chloro-3-pyridyl)-1,2,2-tricyano-4-pentene represented by the following formula (hereinafter referred to as the present invention compound (2)).

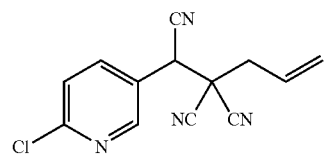

Yield 71%

$^1$H-NMR (CDCl$_3$, TMS, δ (ppm)): 2.99(1H, dd), 3.11(1H, dd), 4.30(1H, s), 5.58–5.68(2H, m), 5.85–6.07(1H, m), 7.54(1H, d), 7.96(1H, dd), 8.54(1H, d)

PRODUCTION EXAMPLE 3

By using (3,4,4-trifluoro-3-butenyl)malononitrile (0.21 g), N,N-dimethylformamide (5 ml), sodium hydride (60% in oil, 0.05 g) and 3-bromomethyl-6-chloropyridine (0.28 g) according to the similar method described in Production Example 1 was obtained 0.22 g of 2-((6-Chloro-3-pyridyl)methyl)-2-(3,4,4-trifluoro-3-butenyl)malononitrile represented by the following formula (the present invention compound (3)).

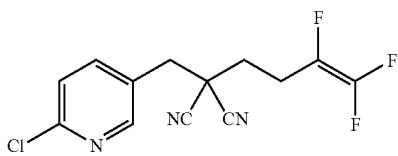

Yield 61%
$^1$H-NMR (CDCl$_3$, TMS, δ (ppm)): 2.22–2.27(2H, m), 2.70-2.80(2H, m), 3.26(2H, s), 7.43(1H, d), 7.74(1H, dd), 8.41(1H, d)

PRODUCTION EXAMPLE 4

(3,3,3-Trifluoropropyl)malononitrile (0.6 g) and 2-chloro-5-chloromethylpyridine (0.6 g) were dissolved in N,N-dimethylformamide (15 ml), potassium carbonate (0.51 g) was added thereto, and the mixture was stirred overnight at room temperature. Then, to the reaction mixture was added water, and extracted with ethyl acetate. The organic layer was washed successively with water, saturated brine, dried over anhydrous magnesium sulfate, and concentrated. The residue obtained was subjected to silica gel column chromatography to give 0.62 g of 2-((6-Chloro-3-pyridyl)methyl)-2-(3,3,3-trifluoropropyl)malononitrile represented by the following formula (hereinafter referred to as the present invention compound (4)).

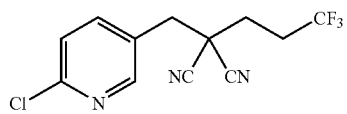

Yield 58%
$^1$H-NMR (CDCl$_3$, TMS, δ (ppm)): 2.25–2.35(2H, m), 2.51–2.60(2H, m), 3.27(2H, s), 7.44(1H, d), 7.74(1H, dd), 8.42(1H, d)

PRODUCTION EXAMPLE 5

2-(Chloromethyl)pyridine hydrochloride (303 mg) was suspended in N,N-dimethylformamide (3 ml), potassium carbonate (256 mg) was added thereto, and the mixture was stirred. Then, to the suspension was added a solution of (3,3,3-trifluoropropyl)malononitrile (300 mg) in N,N-dimethylformamide (3 ml), and further thereto was added potassium carbonate (256 mg), followed by stirring overnight at room temperature. To the reaction mixture was added water, and extracted with ethyl acetate. The organic layer was washed successively with water and saturated brine, dried over anhydrous magnesium sulfate, and concentrated under reduced pressure. The residue obtained was subjected to silica gel column chromatography to give 270 mg of 2-((2-pyridyl)methyl)-2-(3,3,3-trifluoropropyl)malononitrile represented by the following formula (hereinafter referred to as the present invention compound (5)).

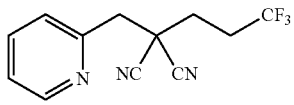

Yield 58%
$^1$H-NMR (CDCl$_3$, TMS, δ (ppm)): 2.33–2.37(2H, m), 2.54–2.65(2H, m), 3.47(2H, s), 7.31–7.37(2H, m), 7.74–7.78(1H, m), 8.64–8.66(1H, m)

PRODUCTION EXAMPLE 6

(3,3,3-Trifluoropropyl)malononitrile (407 mg) was dissolved in N,N-dimethylformamide (5 ml), and potassium carbonate (347 mg) was added thereto, and then, a solution of 3-(chloromethyl)pyridine (320 mg) in N,N-dimethylformamide (1 ml) was added dropwise to the mixture, followed by stirring overnight at room temperature. To the reaction mixture was added water, and extracted with ethyl acetate. The organic layer was washed successively with water and saturated brine, dried over anhydrous magnesium sulfate, and concentrated under reduced pressure. The residue obtained was subjected to silica gel column chromatography to give 400 mg of 2-((3-pyridyl)methyl)-2-(3,3,3-trifluoropropyl)malononitrile represented by the following formula (hereinafter referred to as the present invention compound (6)).

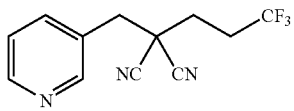

Yield 63%
$^1$H-NMR (CDCl$_3$, TMS, δ (ppm)): 2.25–2.29(2H, m), 2.51–2.62(2H, m), 3.29(2H, s), 7.38–7.42(1H, m), 7.76–7.79(1H, m), 8.64(1H, d), 8.70(1H, dd)

PRODUCTION EXAMPLE 7

By using (3,3,3-trifluoropropyl)malononitrile (401 mg), N,N-dimethylformamide (6 ml), potassium carbonate (0.68 g) and 4-(chloromethyl)pyridine (406 mg) according to the similar method described in Production Example 4 was obtained 500 mg of 2-(4-pyridylmethyl)-2-(3,3,3-trifluoropropyl)malononitrile represented by the following formula (hereinafter referred to as the present invention compound (7)).

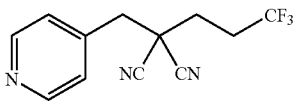

Yield 80%
$^1$H-NMR (CDCl$_3$, TMS, δ (ppm)): 2.25–2.29(2H, m), 2.49–2.62(2H, m), 3.25(2H, s), 7.33(2H, dd), 8.72(2H, dd)

PRODUCTION EXAMPLE 8

By using (3,3,3-trifluoropropyl)malononitrile (226 mg), N,N-dimethylformamide (5 ml), potassium carbonate (193 mg) and 2-(bromomethyl)-6-chloropyridine (335 mg) according to the similar method described in Production Example 4 was obtained 365 mg of 2-((6-chloro-2-pyridyl)methyl)-2-(3,3,3-trifluoropropyl)malononitrile represented by the following formula (the present invention compound (8)).

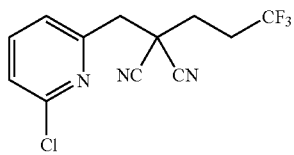

Yield 91%
$^1$H-NMR (CDCl$_3$, TMS, δ (ppm)): 2.33–2.37(2H, m), 2.54–2.65(2H, m), 3.43(2H, s), 7.32(1H, d), 7.38(1H, d), 7.74(1H, dd)

PRODUCTION EXAMPLE 9

By using (3,3,3-trifluoropropyl)malononitrile (83 mg), N,N-dimethylformamide (10 ml), potassium carbonate (71 mg) and 3-(chloromethyl)-6-(trifluoromethyl)pyridine (100 mg) according to the similar method described in Production Example 4 was obtained 130 mg of 2-((6-(trifluoromethyl)-3-pyridyl)methyl)-2-(3,3,3-trifluoropropyl)malononitrile represented by the following formula (hereinafter referred to as the present invention compound (9)).

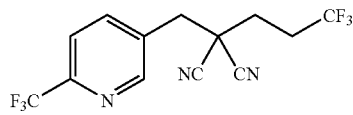

Yield 79%
$^1$H-NMR (CDCl$_3$, TMS, δ (ppm)): 2.29–2.34(2H, m), 2.53–2.68(2H, m), 3.36(2H, s), 7.79(1H, d), 7.98(1H, dd), 8.76(1H, d)

PRODUCTION EXAMPLE 10

By using (3,3,3-trifluoropropyl)malononitrile (3.6 g), dimethylsulfoxide (20 ml), potassium carbonate (3.0 g) and 6-bromo-3-(bromomethyl)pyridine (5.5 g) according to the similar method described in Production Example 4 was obtained 2.2 g of 2-((6-bromo-3-pyridyl)methyl)-2-(3,3,3-trifluoropropyl)malononitrile represented by the following formula (hereinafter referred to as the present invention compound (10)).

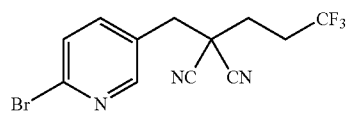

Yield 31%
$^1$H-NMR (CDCl$_3$, TMS, δ(ppm)): 2.26–2.29(2H, m), 2.48–2.62(2H,m),3.27(2H,s),7.59(1H,d),7.63(1H,dd),8.40(1H,d)

PRODUCTION EXAMPLE 11

In 10 ml of dry diethylamine was dissolved 2.0 g or the present invention compound (10). To the solution were added successively (trimethylsilyl)acetylene (3.0 g), copper (I) iodide (12 mg), triphenylphosphine (70 mg) and dichlorobis(triphenylphosphine)palladium (105 mg) under nitrogen atmosphere. The mixture was stirred at room temperature for 3 hours, further stirred at 50° C. for 5 hours. The reaction mixture was concentrated under reduced pressure. The residue was subjected to silica gel column chromatography to give 660 mg of 2-(3,3,3-trifluoropropyl)-2-((6-(trimetylsilyl)ethynyl-3-pyridyl)methyl)malononitrile (hereinafter referred to as the intermediate A).

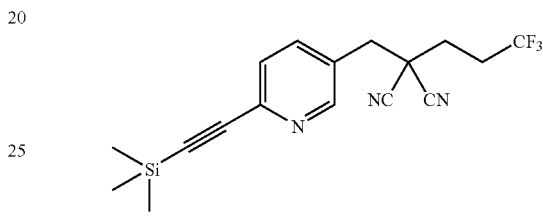

Yield 32%
$^1$H-NMR (CDCl$_3$, TMS, δ(ppm)): 0.28(9H, s), 2.22–2.27 (2H, m), 2.49–2.61(2H, m), 3.28(2H, s), 7.53(1H, d), 7.72 (1H, dd), 8.57(1H, d)

Next, 660 mg of the intermediate A was dissolved in tetrahydrofuran (15 ml), and hydrate of tetra-n-butylammonium fluoride (200 mg) was added thereto. The mixture was stirred at room temperature for 30 minutes, to the reaction mixture was added water. The mixture was extracted with ethyl acetate. The organic layer was washed successively with water, saturated brine, dried over anhydrous magnesium sulfate, and concentrated. The residue was subjected to silica gel chromatography to give 130 mg of 2-((6-ethynyl-3-pyridyl)methyl)-2-(3,3,3-trifluoropropyl)malononitrile (hereinafter referred to as the present invention compound (11)).

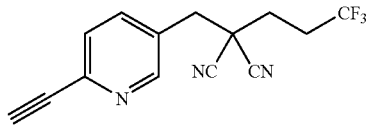

Yield 25%
$^1$H-NMR (CDCl$_3$, TMS, δ(ppm)): 2.25–2.29(2H, m), 2.51–2.60(2H, m), 3.25(1H, s), 3.29(2H, s), 7.58(1H, d), 7.76(1H, dd), 8.61(1H, d)

PRODUCTION EXAMPLE 12

In N-methyl-2-pyrrolidinone (15 ml) was dissolved 664 mg of the present invention compound (10), and copper(I) cyanide (267 mg) was added thereto. The mixture was stirred at 180° C. for 3 hours, to the reaction mixture was added water. The mixture was extracted with ethyl acetate. The organic layer was washed successively with water, saturated brine, dried over anhydrous magnesium sulfate, and concentrated. The residue was subjected to silica gel column chromatography to give 200 mg of 2-((6-cyano-3-pyridyl)methyl)- 2-(3,3,3-trifluoropropyl)malononitrile (hereinafter, referred to as the present invention compound (12)).

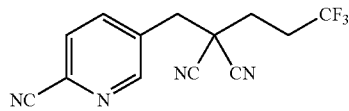

Yield 36%
$^1$H-NMR (CDCl$_3$, TMS,δ(ppm)): 2.30–2.35(2H, m), 2.54–2.64(2H, m), 3.35(2H, s), 7.80(1H, d), 7.94(1H, dd), 8.76(1H, d)

PRODUCTION EXAMPLE 13

By using (3,3,3-trifluoropropyl)malononitrile (5.8 g), dimethylsulfoxide (20 ml), potassium carbonate (4.8 g) and 6-fluoro-3-(bromomethyl)pyridine (6.7 g) according to the similar method described in Production Example 4 was obtained 3.3 g of 2-((6-fluoro-3-pyridyl)methyl)-2-(3,3,3-trifluoropropyl)malononitrile represented by the following formula (hereinafter referred to as the present invention compound (13)).

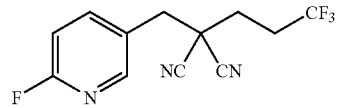

Yield 35%
$^1$H-NMR(CDCl$_3$,TMS,δ(ppm)): 2.26–2.30(2H, m), 2.51–2.63(2H, m), 3.28(2H, s), 7.05(1H, dd), 7.88(1H, m), 8.26(1H, d)

PRODUCTION EXAMPLE 14

By using (3,3,3-trifluoropropyl)malononitrile (540 mg), N,N-dimethylformamide (4 ml), potassium carbonate (400 mg) and 6-bromo-2-(bromomethyl)pyridine (590 mg) according to the similar method described in Production Example 4 was obtained 541 mg of 2-((6-bromo-2-pyridyl)methyl)-2-(3,3,3-trifluoropropyl)malononitrile represented by the following formula (hereinafter referred to as the present invention compound (14)).

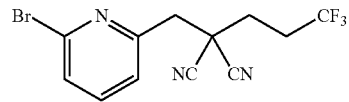

Yield 59%
$^1$H-NMR (CDCl$_3$, TMS, δ(ppm)): 2.33–2.37(2H, m), 2.54–2.65(2H, m), 3.43(2H, s), 7.35(1H, d), 7.54(1H, d), 7.63(1H, dd)

PRODUCTION EXAMPLE 15

By using (3,3,3-trifluoropropyl)malononitrile (480 mg), N,N-dimethylformamide (6 ml), potassium carbonate (420 mg) and 5,6-dichloro-3-(bromomethyl)pyridine (720 mg) according to the similar method described in Production Example 4 was obtained 698 mg of 2-((5,6-dichloro-3-pyridyl)methyl)-2-(3,3,3-trifluoropropyl)malononitrile represented by the following formula (hereinafter referred to as the present invention compound (15)).

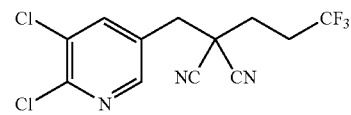

Yield 73%
$^1$H-NMR (CDCl$_3$, TMS, δ(ppm)): 2.27–2.32(2H, m), 2.52–2.64(2H, m), 3.26(2H, s), 7.87(1H, d), 8.34(1H, d)

Production examples of intermediate compounds are here exemplified as Reference Production Example.

REFERENCE PRODUCTION EXAMPLE 1

0.18 g of a compound represented by the formula:

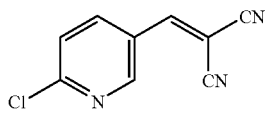

was dissolved in ethanol (1 ml), and a solution in which 40 mg of sodium borohydride was suspended in 1 ml of ethanol was added dropwise to the above solution with stirring at room temperature. The reaction mixture was stirred for 30 minutes at room temperature, and then a saturated aqueous solution of ammonium chloride was added thereto, followed by extracting with ethyl acetate. The organic layer was washed with saturated brine, dried over anhydrous magnesium sulfate, and concentrated under reduced pressure. The residue obtained was subjected to silica gel column chromatography to give 0.12 g of ((6-Chloro-3-pyridyl)methyl) malononitrile (intermediate (1)).

Yield 66%

REFERENCE PRODUCTION EXAMPLE 2

Malononitrile (6.98 g), tetrabutylammonium bromide (681 mg) and 4-bromo-1,1,2-trifluoro-1-butene (10.0 g) were mixed, and to the mixture was added potassium t-butoxide (5.92 g) with stirring at 0° C. under nitrogen atmosphere, followed by stirring for 12 hrs at room temperature. Then the reaction mixture was added to water, and extracted with t-butyl methyl ether. The organic layer was washed with water and saturated brine, dried over anhydrous magnesium sulfate, and concentrated under reduced pressure. The residue obtained was subjected to silica gel column chromatography to give 1.31 g of (3,4,4-trifluoro-3-butenyl)malononitrile (intermediate (2)).

Yield 14%

REFERENCE PRODUCTION EXAMPLE 3

Malononitrile (27.6 g) was dissolved in N,N-dimethylformamide (50 ml), and potassium carbonate (27.6 g) was added thereto. The reaction mixture was stirred for one hour, and 1-bromo-3,3,3-trifluoropropane (17.7 g) which was dissolved in N,N-dimethylformamide (20 ml) was added dropwise thereto, followed by stirring for one hour. Then to the reaction mixture was added water, and extracted with diethyl ether. The organic layer was washed successively with water and saturated brine, dried over anhydrous magnesium sulfate, and concentrated under reduced pressure. The residue obtained was subjected to silica gel column chromatography to give 11.3 g of (3,3,3-trifluoropropyl)malononitrile (intermediate (3)).

Yield 68%

The intermediate compounds used for a production of compound were exemplified together with compound number and physical property value below.

Intermediate (1)

((6-Chloro-3-pyridyl)methyl)malononitrile

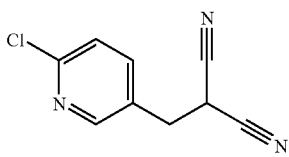

mp. 63.0° C.

Intermediate (2)

(3,4,4-trifluoro-3-butenyl)malononitrile

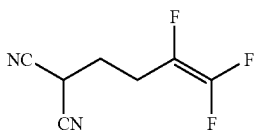

$^1$H-NMR (CDCl$_3$, TMS, δ (ppm)): 1.18–1.28(1H, m), 2.27–2.34(2H, m), 2.58–2.72(2H, m), 3.88(1H, t)

Intermediate (3)

(3,3,3-trifluoropropyl)malononitrile

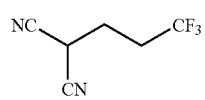

$^1$H-NMR (CDCl$_3$, TMS, δ (ppm)): 2.32–2.42(2H, m), 2.43–2.52(2H, m), 3.91(1H, t)

Specific examples of the present invention compounds are listed together with their compound numbers in Table 1.

TABLE 1

(I)

| Compound Number | R$^1$ | R$^2$ | R$^3$ | R$^4$ | (R$^5$)$_n$ | bonding site* |
|---|---|---|---|---|---|---|
| 1 | H | H | H | CH=CH$_2$ | 6-Cl | 3 |
| 2 | H | CN | H | CH=CH$_2$ | 6-Cl | 3 |
| 3 | H | H | H | CH$_2$CF=CF$_2$ | 6-Cl | 3 |
| 4 | H | H | H | CH$_2$CF$_3$ | 6-Cl | 3 |
| 5 | H | H | H | CH$_2$CF$_3$ | — | 2 |
| 6 | H | H | H | CH$_2$CF$_3$ | — | 3 |
| 7 | H | H | H | CH$_2$CF$_3$ | — | 4 |
| 8 | H | H | H | CH$_2$CF$_3$ | 6-Cl | 2 |
| 9 | H | H | H | CH$_2$CF$_3$ | 6-CF$_3$ | 3 |
| 10 | H | H | H | CH$_2$CF$_3$ | 6-Br | 3 |
| 11 | H | H | H | CH$_2$CF$_3$ | 6-C≡CH | 3 |
| 12 | H | H | H | CH$_2$CF$_3$ | 6-CN | 3 |
| 13 | H | H | H | CH$_2$CF$_3$ | 6-F | 3 |
| 14 | H | H | H | CH$_2$CF$_3$ | 6-Br | 3 |
| 15 | H | H | H | CH$_2$CF$_3$ | 5-Cl, 6-Cl | 3 |
| 16 | H | H | H | CH$_2$CH=CH$_2$ | 6-Cl | 3 |
| 17 | H | H | H | CH=C(Me)$_2$ | 6-Cl | 3 |
| 18 | H | H | H | CH=CF$_2$ | 6-Cl | 3 |
| 19 | H | H | H | CH$_2$CH=CF$_2$ | 6-Cl | 3 |
| 20 | H | H | H | C(CF$_3$)=CH$_2$ | 6-Cl | 3 |
| 21 | H | H | H | CH=CH(CF$_3$) | 6-Cl | 3 |
| 22 | H | H | H | CH$_2$F | 6-Cl | 3 |
| 23 | H | H | H | CH$_2$CHF$_2$ | 6-Cl | 3 |
| 24 | H | H | H | CF$_2$CF$_3$ | 6-Cl | 3 |
| 25 | H | H | H | CH$_2$CH$_2$CF$_3$ | 6-Cl | 3 |
| 26 | H | H | H | CH$_2$CF$_2$CF$_3$ | 6-Cl | 3 |
| 27 | H | H | H | 2,2-dichloro-1-cyclopropyl | 6-Cl | 3 |
| 28 | H | H | H | cyclobutyl | 6-Cl | 3 |
| 29 | H | H | H | cyclopropyl | 6-Cl | 3 |
| 30 | H | Me | H | CH$_2$CF$_3$ | 6-Cl | 3 |
| 31 | Me | Me | H | CH$_2$CF$_3$ | 6-Cl | 3 |
| 32 | H | H | H | CH$_2$CF$_3$ | 6-(1,1-dimethylethyl) | 3 |
| 33 | H | Me | H | CH$_2$CF$_3$ | 6-(1,1-dimethylethyl) | 3 |
| 34 | Me | Me | H | CH$_2$CF$_3$ | 6(1,1-dimethylethyl) | 3 |
| 35 | H | H | H | CH$_2$CF$_3$ | 6-(1,1-dimethylethyl) | 2 |
| 36 | H | Me | H | CH$_2$CF$_3$ | 6-(1,1-dimethylethyl) | 2 |
| 37 | Me | Me | H | CH$_2$CF$_3$ | 6-(1,1-dimethylethyl) | 2 |
| 38 | H | H | H | CH$_2$CF$_3$ | 2-(1,1-dimethylethyl) | 4 |
| 39 | H | Me | H | CH$_2$CF$_3$ | 2-(1,1-dimethylethyl) | 4 |
| 40 | Me | Me | H | CH$_2$CF$_3$ | 2-(1,1-dimethylethyl) | 4 |
| 41 | H | H | H | CH$_2$CF$_3$ | 4-CF$_3$ | 2 |
| 42 | H | H | H | CH$_2$CF$_3$ | 4-CN | 2 |
| 43 | H | H | H | CH$_2$CF$_3$ | 4-NO$_2$ | 2 |
| 44 | H | H | H | CH$_2$CF$_3$ | 4-Br | 2 |
| 45 | H | H | H | CH$_2$CF$_3$ | 4-Cl | 2 |
| 46 | H | H | H | CH$_2$CF$_3$ | 5-CF$_3$ | 2 |
| 47 | H | H | H | CH$_2$CF$_3$ | 5-CN | 2 |
| 48 | H | H | H | CH$_2$CF$_3$ | 5-NO$_2$ | 2 |
| 49 | H | H | H | CH$_2$CF$_3$ | 5-Br | 2 |
| 50 | H | H | H | CH$_2$CF$_3$ | 5-Cl | 2 |
| 51 | H | H | H | CH$_2$CF$_3$ | 5-F | 2 |
| 52 | H | H | H | CH$_2$CF$_3$ | 6-CF$_3$ | 2 |
| 53 | H | H | H | CH$_2$CF$_3$ | 6-CN | 2 |
| 54 | H | H | H | CH$_2$CF$_3$ | 6-NO$_2$ | 2 |
| 55 | H | H | H | CH$_2$CF$_3$ | 6-F | 2 |
| 56 | H | H | H | CH$_2$CF$_3$ | 5-CF$_3$ | 3 |
| 57 | H | H | H | CH$_2$CF$_3$ | 5-CN | 3 |

TABLE 1-continued $$\text{(I)}$$

(structure: pyridine ring with positions labeled 2,3,4,5,6 and N at 1; $(R^5)_n$ on pyridine; attached to C($R^1$)($R^2$)–C(CN)(CN)–C($R^3$)($R^4$))

| Compound Number | $R^1$ | $R^2$ | $R^3$ | $R^4$ | $(R^5)_n$ | bonding site* |
|---|---|---|---|---|---|---|
| 58 | H | H | H | $CH_2CF_3$ | 5-$NO_2$ | 3 |
| 59 | H | H | H | $CH_2CF_3$ | 5-Br | 3 |
| 60 | H | H | H | $CH_2CF_3$ | 5-Cl | 3 |
| 61 | H | H | H | $CH_2CF_3$ | 5-F | 3 |
| 62 | H | H | H | $CH_2CF_3$ | 2-$CF_3$ | 4 |
| 63 | H | H | H | $CH_2CF_3$ | 2-CN | 4 |
| 64 | H | H | H | $CH_2CF_3$ | 2-Br | 4 |
| 65 | H | H | H | $CH_2CF_3$ | 2-Cl | 4 |
| 66 | H | H | H | $CH_2CF_3$ | 2-F | 4 |
| 67 | H | H | H | $CH_2CF_3$ | 5-F, 6-F | 3 |
| 68 | H | H | H | $CH_2CF_3$ | 5-Cl, 6-F | 3 |
| 69 | H | H | H | $CH_2CF_3$ | 5-F, 6-Cl | 2 |
| 70 | H | H | H | $CH_3$ | 6-Cl | 2 |

*position on pyridine ring at which the carbon atom bonded to $R^1$ and $R^2$ is bonded.

Formulation Examples are exemplified below. In addition, "part" means a part by weight. The present invention compounds are designated by their compound numbers shown in Tables 1.

FORMULATION EXAMPLE 1

9 parts of each of the present invention compounds (1) to (70) are dissolved in 37.5 parts of xylene and 37.5 parts of dimethylformamide, and 10 parts of polyoxyethylene styryl phenyl ether and 6 parts of calcium dodecylbenzenesulfonate are added thereto, followed by well stirring and mixing, to give an emulsion for each compound.

FORMULATION EXAMPLE 2

To 40 parts of each of the present invention compounds (1) to (70) are added 5 parts of SORPOL 5060 (registered trade name for TOHO KAGAKU KOGYO), followed by well mixing. To the mixture are added 32 parts of CARPLEX #80 (registered trade name for SHIONOGI & Co., synthetic hydrated silicone oxide fine powder) and 23 parts of 300 mesh diatomaceous earth, followed by mixing with juice mixer, to give a wettable powder for each compound.

FORMULATION EXAMPLE 3

To 3 parts of each of the present invention compounds (1) to (70) are added 5 parts of synthetic hydrated silicon oxide fine powder, 5 parts of sodium dodecylbenzenesulfonate, 30 parts of bentonite, and 57 parts of clay, followed by well stirring and mixing. Then an appropriate amount of water is added to this mixture, followed by further stirring, granulating with a granulator, and air drying, to give a granule for each compound.

FORMULATION EXAMPLE 4

4.5 Parts of each of the present invention compounds (1) to (70), 1 part of synthetic hydrated silicon oxide fine powder, 1 part of Doriresu B (Sankyo Co., Ltd.) as a flocculant and 7 parts of clay are well mixed with a mortar, followed by stirring and mixing with a juice mixer. To the resulting mixture is added 86.5 parts of cut clay, followed by well stirring and mixing, to give a powder for each compound.

FORMULATION EXAMPLE 5

10 Parts of each of the present invention compounds (1) to (70), 35 parts of white carbon containing 50 parts of polyoxyethylene alkyl ether-sulfate ammonium salt and 55 parts of water are mixed and pulverized by the wet grinding method to give a formulation for each compound.

FORMULATION EXAMPLE 6

0.5 Parts of each of the present invention compounds (1) to (70) are dissolved in 10 parts of dichloromethane, and the resulting solution is mixed with 89.5 parts of Iso-Par M (isoparaffine: registered trade name for EXXON CHEMICAL LTD) to give an oil solution.

FORMULATION EXAMPLE 7

0.1 Parts of each of the present invention compounds (1) to (70) and 49.9 parts of NEO-CHIOZOL (CHUO KASEI Co., LTD) are charged into aerosol can, and aerosol valve is fixed to the can. Then 25 parts of dimethyl ether and 25 parts of LPG are filled in the can, followed by shaking and fitting an actuator on it, to give an oil aerosol.

FORMULATION EXAMPLE 8

0.6 Parts of each of the present invention compounds (1) to (70), 0.01 parts of BHT, 5 parts of xylene, 3.39 parts of deodorized kerosene and 1 part of emulsifier [Atmos 300 (registered trade name for ATMOS CHEMICAL LTD)] are mixed and dissolved. The solution obtained and 50 parts of distilled water are charged into aerosol container, and a valve is fixed to the container. 40 Parts of propellant (LPG) are charged under pressure through the valve to give an aqueous aerosol.

The following test example will demonstrate that the present invention compounds have an excellent pesticidal activity as active ingredient of a composition for controlling pests. The present invention compounds are designated by their compound numbers shown in Tables 1.

TEST EXAMPLE 1

The formulation obtained according to Formulation Example 5 using the present invention compounds (3), (4), (5), (7), (8), (9), (10), (11), (12), (13), (14) and (15) respectively, was diluted with water so that the active ingredient concentration came to 500 ppm to prepare a pesticidal solution for test.

Fifty grams of molding Bonsoru 2 (available from Sumitomo Chemical Co., Ltd.) was put into a polyethylene cup, and 10 to 15 seeds of rice were planted in the polyethylene cup. Then rice plants were grown until the second foliage leaves developed and then cut into the same height of 5 cm. The pesticidal solution for test prepared above was sprayed at the rate of 20 ml/cup to these rice plants. After the pesticidal solution sprayed onto the rice plants were dried, they were put into a plastic cup for escape prevention of test pests, and thirty first-instar larvae of *Nilaparvata lugens* were set free on the rice plants, followed by covering the plastic cup with a lid. Then the plastic cup was left in a greenhouse (25° C.). On the sixth day after the release of larvae of *Nilaparvata lugens,* the number of parasitic *Nilaparvata lugens* on the rice plants was examined.

As a result, in the treatment with each of the present invention compounds (3), (4), (5), (7), (8), (9), (10), (11), (12), (13), (14) and (15), the number of parasitic *Nilaparvata lugens* was not greater than 3.

TEST EXAMPLE 2

The formulation obtained according to Formulation Example 5 using the present invention compounds (4), (8), (9), (10), (11), (12) and (13) respectively, was diluted with water so that the active ingredient concentration came to 500 ppm to prepare a pesticidal solution for test.

A polyethylene cup was seeded with cucumber and a plant was grown until the first true leaf was developed, on which about twenty *Aphis gossypii* are allowed to be parasitic. On the next day, the above pesticidal solution for test was sprayed at a ratio of 20 ml/cup to the cucumber plant. On the sixth day after the application, the number of *Aphis gossypii* was examined.

As a result, in the treatment with each of the present invention compounds (4), (8), (9), (10), (11), (12) and (13), the number of parasitic *Nilaparvata lugens* on the sixth day after the treatment was not greater than 3.

TEST EXAMPLE 3

The formulation obtained according to Formulation Example 5 using the present invention compounds (1), (2), (4), (8), (9), (10), (11), (13), (14) and (15) respectively, was diluted with water so that the active ingredient concentration came to 500 ppm to prepare a pesticidal solution for test.

On the bottom of a polyethylene cup having a diameter of 5.5 cm, a filter paper having the same diameter was laid, and 0.7 ml of the above pesticidal solution for test was added dropwise on the filter paper, followed by putting 30 mg of sucrose on it uniformly as a bait. Ten female *Musca domestics* imagoes were set free in the polyethylene cup and covered it with a lid. After 24 hours, the number of surviving *Musca domestics* was examined and the rate of dead pests was calculated.

As a result, in the treatment with each of the present invention compounds (1), (2), (4), (8), (9), (10), (11), (13), (14) and (15), the rate of dead pests was 90% or more.

TEST EXAMPLE 4

The formulation obtained according to Formulation Example 5 using the present invention compounds (1), (4), (8), (9), (11), (12), (13) and (14) respectively, was diluted with water so that the active ingredient concentration came to 500 ppm to prepare a pesticidal solution for test.

On the bottom of a polyethylene cup having a diameter of 5.5 cm, a filter paper having the same diameter was laid, and 0.7 ml of the above pesticidal solution for test was added dropwise on the filter paper, followed by putting 30 mg of sucrose on it uniformly as a bait. Two male *Blattella germanica* imagoes were set free in the polyethylene cup and covered it with a lid. After 6 days, the number of surviving *Blattella germanica* was examined and the rate of dead pests was calculated.

As a result, in the treatment with each of the present invention compounds (1), (4), (8), (9), (11), (12), (13) and (14), the rate of dead pests was 100%.

TEST EXAMPLE 5

The formulation obtained according to Formulation Example 5 using the present invention compounds (3), (4), (8), (9), (10), (11), (12), (13), (14) and (15) respectively, was diluted with water so that the active ingredient concentration came to 500 ppm to prepare a pesticidal solution for test.

0.7 ml of above pesticidal solution for test was added to 100 ml of ion exchanged water (active ingredient concentration: 3.5 ppm). Twenty last-instar larvae of *Culex pipiens pallens* were set free in the solution. After one day, the number of surviving *Culex pipiens pallens* was examined and the rate of dead pests was calculated.

As a result, in the treatment with each of the present invention compounds (3), (4), (8), (9), (10), (11), (12), (13), (14) and (15), the rate of dead pests was 100%.

The following comparative test will demonstrate. The present invention compound (70) and the contrastive compound A, which is the compound of No. 27 described in JP 10-29966 A1, were used.

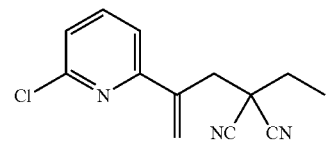

TEST EXAMPLE 6

The formulation obtained according to Formulation Example 5 using the present invention compound (70) and the contrastive compound A, was diluted with water so that the active ingredient concentration came to 2000 ppm to prepare a pesticidal solution for test.

Fifty grams of molding Bonsoru 2 (available from Sumitomo Chemical Co., Ltd.) was put into a polyethylene cup, and 10 to 15 seeds of rice were planted in the polyethylene cup. Then rice plants were grown until the second foliage leaves developed and then cut into the same height of 5 cm. The pesticidal solution for test prepared above was sprayed at the rate of 20 ml/cup to these rice plants. After the pesticidal solution sprayed onto the rice plants were dried, they were put into a plastic cup for escape prevention of test pests, and thirty first-instar larvae of *Nilaparvata lugens* were set free on the rice plants, followed by covering the plastic cup with a lid. Then the plastic cup was left in a greenhouse (25° C.). On the sixth day after the release of larvae of *Nilaparvata lugens,* the number of parasitic *Nilaparvata lugens* on the rice plants was examined.

As a result, in the treatment with the present invention compound (70), the number of parasitic *Nilaparvata lugens* was not greater than 3. In the treatment with the contrastive compound A, the number of parasitic *Nilaparvata lugens* was XX.

INDUSTRIAL APPLICABILITY

Pests such as insect pests, acarine pests, nematode pests and the like can be controlled effectively by the present invention.

The invention claimed is:

1. A malononitrile compound represented by the formula (I):

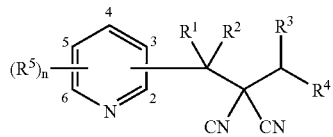

wherein, $R^1$ represents a C1 to C5 (halo)alkyl, a C2 to C5 (halo)alkenyl, a C2 to C5 (halo)alkynyl or a hydrogen atom; $R^2$ represents a C1 to C5 (halo)alkyl, a C1 to C5 (halo)alkyloxy, a C2 to C5 (halo)alkenyl, a C2 to C5 (halo)alkynyl, hydrogen atom or a cyano; $R^3$ and $R^4$ are the same or different and are a C1 to C6 (halo)alkyl, a C2 to C6 (halo)alkenyl, a C2 to C6 (halo)alkynyl, a C3 to C6 (halo)cycloalkyl, a C4 to C6 (halo)cycloalkenyl or a hydrogen atom, or $R^3$ and $R^4$ together may form a C2 to C6 (halo)alkylene or a C4 to C6 (halo)alkenylene; $R^5$ represents a halogen atom, a cyano, a nitro, a C1 to C4 (halo)alkyl, a C2 to C4 (halo)alkenyl, a C2 to C4 (halo)alkynyl, a C1 to C4 (halo)alkyloxy, a C1 to C4 (halo)alkylthio, a C1 to C4 (halo)alkylsulfinyl, a C1 to C4 (halo)alkylsulfonyl, a C2 to C4 (halo)alkylcarbonyl, a C2 to C4 (halo)alkyloxycarbonyl, a C2 to C4 (halo)alkylcarbonyloxy, a phenyloxy or a phenylthio (the above-mentioned phenyloxy and phenylthio may be substituted with a halogen atom or a C1 to C3 alkyl); n is an integer of 0 to 4 and when n is 2 or more, $R^5$ may be the same or different.

2. A pesticide composition comprising the malononitrile compound according to claim 1 as active ingredient and an inert carrier.

3. A method for controlling pests comprising applying an effective dose of the malononitrile compound according to claim 1 to pests or habitat of pests.

* * * * *